United States Patent [19]
Barringer et al.

[11] Patent Number: 5,945,445
[45] Date of Patent: Aug. 31, 1999

[54] COMPOSITION AND METHOD FOR PREVENTING OR TREATING PINE WILTING DISEASE

[75] Inventors: George F. Barringer, Chatham, N.J.; Tetsuo Kumagai, Ikoma, Japan

[73] Assignee: Merck & Co., Inc., Rahway, N.J.

[21] Appl. No.: 09/109,190

[22] Filed: Jul. 2, 1998

Related U.S. Application Data

[63] Continuation of application No. 08/693,183, filed as application No. PCT/JP95/00153, Feb. 6, 1995, abandoned.

[30] Foreign Application Priority Data

Feb. 7, 1994 [JP] Japan ........................... 6-13462

[51] Int. Cl.$^6$ ............................. A01N 43/16; A01N 55/00
[52] U.S. Cl. .................................. 514/453; 514/63
[58] Field of Search ......................... 514/453, 63

[56] References Cited

U.S. PATENT DOCUMENTS

| | | | |
|---|---|---|---|
| 4,199,569 | 4/1980 | Chabala et al. | 424/180 |
| 4,310,519 | 1/1982 | Schonberg et al. | 424/181 |

FOREIGN PATENT DOCUMENTS

| | | |
|---|---|---|
| 0089202 | 9/1983 | European Pat. Off. |
| 0214731 | 3/1987 | European Pat. Off. |

OTHER PUBLICATIONS

Ontoguro et al, Journal of Antibiotics, vol. 41, No. 4 (1988) Screening for New Nematocidal Substances of Microbial Origin by a New Method Using the Pine Wood Nematode; pp. 573–575.

*Primary Examiner*—Allen J. Robinson
*Attorney, Agent, or Firm*—J. Eric Thies; David L. Rose

[57] ABSTRACT

There is disclosed a composition for preventing wilting of pines which comprises as an active ingredient a compound of the formula (I):

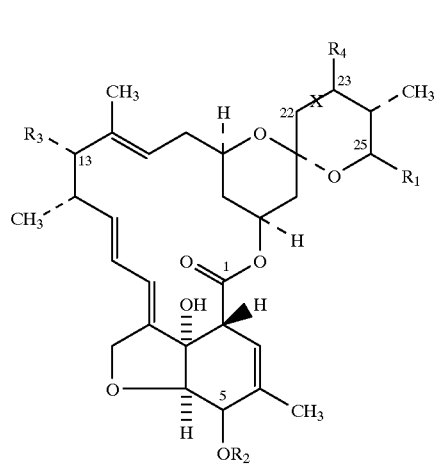

wherein
$R_1$ is alkyl, cycloalkyl or alkenyl;
$R_2$ is hydrogen, alkyl, alkanoyl or alkylsilyl;
$R_3$ is hydrogen or optionally substituted hydroxyl;
$R_4$ is hydrogen, hydroxyl or alkoxyimino;
the carbon-carbon bond X represents a single bond or double bond, provided that, when $R_4$ is alkoxyimino, X represents a single bond, and when $R_1$ is methyl or ethyl and $R_2$, $R_3$ and $R_4$ are hydrogen, X represents a double bond; or a salt thereof, as well as a method of preventing the pine wilt using the same.

Even if pine trees are infected with pine wilt nematodes, the pine wilt nematodes can be killed before the pine wilt nematodes start action in the trunks of the pine trees.

14 Claims, No Drawings

COMPOSITION AND METHOD FOR PREVENTING OR TREATING PINE WILTING DISEASE

This is a continuation of application Ser. No. 08/693,183 filed Aug. 6, 1996, now abandoned, which is a 371 of PCT/JP95/00153, filed Feb. 6, 1995.

FIELD OF THE INVENTION

The present invention relates to a composition for preventing pine wilting disease caused by pine wilt nematode, and also relates to a method for preventing pine wilting disease by using the composition.

BACKGROUND OF THE INVENTION

In summer to the beginning of autumn, pine needles of pines with the pine wilt nematode disease begin to change their color. After about one month, the entire crowns turn red and the pines wilt and die. The pathogen of the pine nematode disease is Bursaphelenchus xylophilus (hereinafter sometimes referred to as pine wilt nematode), which is a kind of nematode. The pine wilt nematode is carried by a Japanese pine sawyer (Monochamus alternatus), which is a kind of longicorn beetles.

In about the middle of May to the end of July, Japanese pine sawyers emerge and get out of pines which suffered from the pine wilt nematode disease the preceding year. The Japanese pine sawyers carry thousands to tens of thousands of pine nematodes in their bodies or on the surface of their bodies, and eat sprigs of healthy pines for maturing (maturation feeding). At this time, the pine nematodes get out of the bodies of the pine sawyers, enter the pine bodies at the injured sites eaten by the Japanese pine sawyers and grow.

After 2 to 3 months, the pines entered by the pine wilt nematodes apparently exhibit wilting and the pine needles change their color. The trees whose pine needles begin to change their color are referred to as abnormal trees. The Japanese pine sawyers matured by the maturation feeding copulate, and then lay eggs in the abnormal trees. The abnormal trees die soon.

The larvae of the pine sawyers can not sometimes hatch in healthy pine trees because the eggs laid in healthy trees are sometimes covered with the resin of the pines. Even if the larvae hatch, they are covered with the resin during feeding under the bark, and die. Thus, the Japanese pine sawyers hardly grow in healthy trees. However, the eggs laid in the dead trees or abnormal trees, which are weakened by the invasion of the pine nematodes, are not covered with the resin, and the larvae hatch out of them and grow by feeding under the bark.

The sufficiently grown larvae of the Japanese pine sawyers make pupal rooms deep in the pines in the end of autumn to the beginning of winter to stay over winter and avoid the cold of winter.

When spring comes and the temperature rises, the larvae of the pine sawyers which have stayed in the pupal rooms become pupae. Soon, the pine sawyers emerge, grow to be imagoes and get out of the dead trees. At this time, the pine nematodes gathered around the pupal rooms transfer to the emerging pine sawyers, and are carried out of the dead trees with the pine sawyers.

While the pine sawyers with the pine nematodes eat healthy sprigs of healthy pines, the pine nematodes get out of the bodies of the pine sawyers and enter the bodies of the pines. Soon, the pines exhibit wilting, and the pine needles begin to change their color. Thus, wilting of pines by the pine nematode disease spreads one after another.

The following methods have been used to prevent wilting of pines by the pine nematode disease.

(a) To lower the density of Japanese pine sawyers:

Pine sawyers are exterminated before the Japanese pine sawyers emerge, mainly at the larval stage. The habitable place of the larvae of the Japanese pine sawyers is restricted to dead trees. The dead trees are felled, the bark is stripped from the trees, and the trees are destroyed by fire or treated with chemicals to exterminate the Japanese pine sawyers. The treatment with chemicals is carried out, for example, by sprinkling organic phosphorus insecticides or carbamate insecticides, or by fumigating with metam ammonium insecticides. Further, methods utilizing insect-parasitic microorganisms or predacious natural enemies or the like have been examined.

(b) Prevention of Japanese pine sawyers from maturation feeding:

Imagoes of pine sawyers can be prevented from maturation feeding to prevent infection of pine nematodes. For this, insecticides are sprinkled before the emergence of the pine sawyers. Insecticides are sprinkled from the ground or dropped from a helicopter.

(c) Prevention of wilting by treating pine trees with chemicals one by one:

Before the infection of the Japanese pine sawyers is likely to happen, chemicals with insecticidal activity are injected into the trunks of pine trees or sprinkled on the soil to exterminate the pine wilt nematodes directly. As the chemicals injected into the trunks of the trees, mesulfenfos, morantel tartrate and levamisole hydrochloride have been used. As the chemicals sprinkled on the soil, ethylthiometon, methomyl, aldicarb and the like were found to be effective but have not yet been used practically.

(d) Breeding of resistant pines:

Expression of induced resistance and the like by selective or combination breeding or with attenuated pine nematodes have been examined to make pines resistant to infection with pine wilt nematodes, and gradually provided results. However, it takes much time to establish the technology.

The above methods for preventing the pine nematode disease have both merits and demerits. The method by felling the dead trees, stripping the bark from the trees and destroying the trees by fire or treating the trees with chemicals to exterminate the Japanese pine sawyers is problematic because of shortage of labor necessary to carry out the method completely.

The method by sprinkle insecticides to prevent Japanese pine sawyers from maturation feeding is effective. However, this method must be carried out with various restrictions depending upon circumstances.

The method by treating pine trees with chemicals one by one has been carried out particularly in places where it is difficult to sprinkle insecticides, for example, shrines, Buddhist temples, parks, towns and the like. However, this method is problematic in terms of damage from the chemicals injected into the trunks of pine trees, stability of the effect, the duration and the like.

Thus, there is still a need for another method for preventing wilting of pines caused by the pine nematode disease.

OBJECTS OF THE INVENTION

The main object of the present invention is to provide a composition with stable activity for preventing wilting of pines caused by the pine wilt nematode disease.

Another object of the present invention is to provide a method of preventing wilting of pines caused by the pine wilt nematode disease.

SUMMARY OF THE INVENTION

The present inventors have intensively studied to achieve the above objects. As a result, it has been found that avermectins or their derivatives have potent insecticidal activity against pine wilt nematodes and Japanese pine sawyers. After further study, the present invention has been completed.

That is, according to the present invention, there is provided (1) a composition for preventing wilting of pines which comprises as an active ingredient a compound of the formula (I):

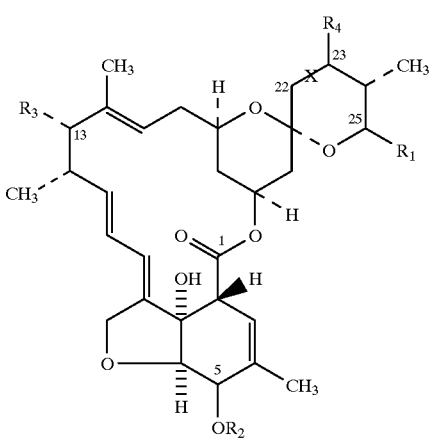

wherein $R_1$ is alkyl, cycloalkyl or alkenyl;

$R_2$ is hydrogen, alkyl, alkanoyl or alkylsilyl;

$R_3$ is hydrogen or optionally substituted hydroxyl;

$R_4$ is hydrogen, hydroxyl or alkoxyimino;

the carbon-carbon bond X represents a single bond or double bond, provided that, when $R_4$ is alkoxyimino, X represents a single bond, and when $R_1$ is methyl or ethyl and $R_2$, $R_3$ and $R_4$ are hydrogen, X represents a double bond; or a salt thereof, (2) A composition according to said (1), wherein $R_1$ is isopropyl or sec-butyl, (3) A composition according to said (1), wherein $R_2$ is hydrogen, (4) A composition according to said (1), wherein $R_3$ is a group of the formula (II) or formula (III):

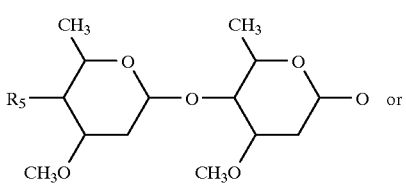

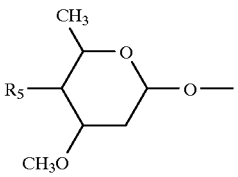

wherein $R_5$ is
oxo;
optionally substituted hydroxyl; or
—$NR_6R_7$ wherein $R_6$ and $R_7$ are each independently hydrogen, lower alkyl, lower alkanoyl, optionally substituted benzenesulfonyl or lower alkylsulfonyl, (5) A composition according to said (4), wherein $R_3$ is a group of the formula (II) wherein $R_5$ is hydroxyl or methylamino, (6) A composition according to said (1), wherein $R_4$ is hydrogen.

(7) A composition according to said (1), wherein $R_1$ is sec-butyl or isopropyl, $R_2$ is hydrogen, $R_3$ is a group of the formula (II) in claim 4 wherein $R_5$ is hydroxyl, $R_4$ is hydrogen, and X is a single bond, (8) A composition according to said (1), wherein $R_1$ is sec-butyl or isopropyl, $R_2$ is hydrogen, $R_3$ is a group of the formula (II) in claim 4 wherein $R_5$ is hydroxyl, $R_4$ is hydrogen, and X is a double bond, (9) A composition according to said (1), wherein $R_1$ is sec-butyl or isopropyl, $R_2$ is hydrogen, $R_3$ is a group of the formula (II) in claim 4 wherein $R_5$ is methylamino, $R_4$ is hydrogen, and X is a double bond,

(10) A composition according to said (1), which is an injectable composition,

(11) A composition according to said (1), which further comprises a surfactant,

(12) A composition according to said (1), which is for preventing the infection with Bursaphelenchus xylophilus or killing Bursaphelenchus xylophilus or *Monochamus alternatus,*

(13) A method of preventing wilting of pines which comprises treating trunks of pines with an effective amount of a compound of the formula (I) in said (1),

(14) A method according to said (13) which comprises treating trunks of pines with a composition of said (1),

(15) A method according to said (13) which comprises treating trunks of pines with a composition of said (11),

(16) A method according to said (15), which comprises injecting a composition of said (11) into trunks of pines.

The compound of the formula (I) and a salt thereof have insecticidal activity against pine wilt nematodes (i.e., *Bursaphelenchus xylophilus*) or Japanese pine sawyers. In particular, ivermectin (compound No.1 in Table 1), abamectin (compound No.2 in Table 1) and emamectin benzoate (compound No.3 in Table 1) have excellent insecticidal activity against both pine wilt nematodes and Japanese pine sawyers. They are therefore more effective in preventing wilting of pines and are important particularly because chemicals conventionally used for injection into trunks of pines have insecticidal activity against pine wilt nematodes but no or weak insecticidal activity against Japanese pine sawyers.

Thus, the above compounds has an excellent insecticidal activity against both nematodes and Japanese pine sawyers, so that it can cope with the prevention of the pine wilt more effectively. Further, even if pine trees are infected with pine wilt nematodes, the pine wilt nematodes can be killed before the pine wilt nematodes start action in the trunks of the pine trees, to prevent wilting of pines caused by the pine wilt nematode disease.

The compounds of the formula (I) are known compounds (JP-B 3-17837; JP-B 2-17558; JP-A 58-167591; Ivermectin and Abamectin by William C. Campbell (1989), Springer-verlag; JP-A 62-29590 and JP-A 62-265288) and have been used or under development as agricultural insecticides and anthelmintic agents for humans and domestic animals. However, it has not been known that these compounds can be used for preventing the pine wilt nematode disease to prevent wilting of pines.

Example of the alkyl represented by $R_1$ and $R_2$ include straight-chain or branched-chain alkyl having 1 to 6 carbon atoms, preferably 1 to 4 carbon atoms, for example, methyl, ethyl, propyl (e.g., isopropyl, etc.), butyl (e.g., sec-butyl, etc.) and the like.

Examples of the cycloalkyl represented by $R_1$ include cycloalkyl having 3 to 8 carbon atoms, preferably 3 to 6 carbon atoms, for example, cyclopropyl, cyclobutyl, cyclopentyl, cyclohexyl and the like.

Examples of the alkenyl represented by $R_1$ include straight-chain or branched-chain alkenyl having 2 to 8 carbon atoms, preferably 2 to 6 carbon atoms, for example, vinyl, propenyl, butenyl (e.g., 1,3-dimethyl-1-butenyl, etc.), pentenyl and the like.

Examples of the alkanoyl represented by $R_2$ include alkanoyl having 2 to 8 carbon atoms, preferably 2 to 4 carbon atoms, for example, acetyl, propionyl, butyryl and the like.

Examples of the alkylsilyl represented by $R_2$ include alkylsilyl containing alkyl described for $R_1$. Among them, t-butyldimethylsilyl is preferred.

Examples of the optionally substituted hydroxyl represented by $R_3$ include hydroxyl; lower alkanoyloxy having 2 to 6 carbon atoms, preferably 2 to 4 carbon atoms (e.g., acetyloxy, propionyloxy, butyryloxy, etc.); a group of the formula (II) or formula (III):

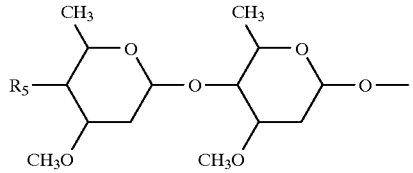

wherein $R_5$ is oxo;

optionally substituted hydroxyl such as hydroxyl, R-COO- {wherein R is optionally substituted $c_{1-8}$ alkyl (e.g., methyl, ethyl, propyl, etc.) (wherein the substituent includes optionally esterified carboxyl and optionally substituted amino), optionally substituted amino (wherein the substituent includes $C_{1-4}$ alkyl (e.g., methyl, ethyl, propyl, etc.)), optionally substituted phenoxy (wherein the substituent includes nitro)} or alkylsilyloxy (e.g., t-butyldimethylsilyloxy, etc.); or —$NR_6R_7$ wherein $R_6$ and $R_7$ are each independently hydrogen, $c_{1-4}$ lower alkyl (e.g., methyl, ethyl, propyl, butyl, etc.), $C_{2-4}$ lower alkanoyl (e.g., acetyl, propionyl, butyryl, etc.), optionally substituted benzenesulfonyl (wherein the substituent includes halogen such as fluorine, chlorine, bromine, iodine) or $C_{1-4}$ lower alkylsulfonyl (e.g., methylsulfonyl, ethylsulfonyl, propylsulfonyl, butylsulfonyl, etc.).

Examples of the alkoxyimino represented by $R_4$ include alkoxyimino having 1 to 6 carbon atoms, preferably 1 to 4 carbon atoms, for example, methoxyimino, ethoxyimino, propoxyimino and the like.

$R_1$ is preferably isopropyl or sec-butyl. $R_2$ is preferably hydrogen. $R_3$ is preferably a group of the formula (II). $R_4$ is preferably hydrogen. $R_5$ is preferably hydroxyl or methylamino.

Examples of the above mentioned salt include salts of inorganic acids such as hydrogen halide acids (e.g., hydrochloric acid, hydrobromic acid, etc.), sulfuric acid and phosphoric acid and salts of organic acids such as acetic acids, propionic acid, oxalic acid, malonic acid and benzoic acid.

Examples of the compound of the formula (I) are shown in Tables 1 to 4.

TABLE 1

| Com- pound No. | Compound | $R_1$ | $R_2$ | $R_3$ | $R_4$ | $R_5$ | X |
|---|---|---|---|---|---|---|---|
| 1 | Ivermectin | sec-butyl iso-propyl | H | 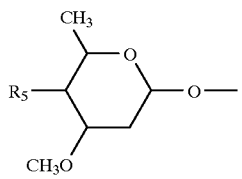 | —H | —OH | single bond |

TABLE 1-continued

| No. | Compound | R₁ | R₂ | R₃ | R₄ | R₅ | X |
|---|---|---|---|---|---|---|---|
| 2 | Abamectin | sec-butyl / iso-propyl | H | " | —H | —OH | double bond |
| 3 | Emamectin benzoate | sec-butyl / iso-propyl | H | " | —H | —NHCH₃ · COOH-C₆H₅ | double bond |
| 4 | Moxidectin | 1,3-dimethyl-1-butenyl | H | H | =NOCH₃ | — | single bond |
| 5 | Doramectin | cyclohexyl | H | (disaccharide structure with R₅, CH₃O, CH₃ groups) | —H | —OH | double bond |
| 6 | Avermectin A1a | sec-butyl | CH₃ | " | —H | —OH | double bond |
| 7 | Avermectin A1b | iso-propyl | CH₃ | " | —H | —OH | double bond |
| 8 | Avermectin A2a | sec-butyl | CH₃ | " | —OH | —OH | single bond |

TABLE 2

| No. | Compound | R₁ | R₂ | R₃ | R₄ | R₅ | X |
|---|---|---|---|---|---|---|---|
| 9 | Avermectin A2b | iso-propyl | CH₃ | (disaccharide structure with R₅, CH₃O, CH₃ groups) | —OH | —OH | single bond |
| 10 | Avermectin B2a | sec-butyl | H | " | —OH | —OH | single bond |
| 11 | Avermectin B2b | iso-propyl | H | " | —OH | —OH | single bond |
| 12 | other derivative | sec-butyl | H | " | —H | CH₃COO— | double bond |
| 13 | other derivative | sec-butyl | CH₃CO | " | " | —OH | double bond |
| 14 | other derivative | sec-butyl | " | " | " | CH₃COO— | double bond |
| 15 | other derivative | sec-butyl | Si(CH₃)₂C(CH₃)₃ | " | " | —OH | double bond |
| 16 | other derivative | sec-butyl | " | " | " | —OSi(CH₃)₂C(CH₃)₃ | double bond |

TABLE 2-continued

| No. | Compound | $R_1$ | $R_2$ | $R_3$ | $R_4$ | $R_5$ | X |
|---|---|---|---|---|---|---|---|
| 17 | other derivative | sec-butyl | " | " | " | $(CH_3)_3CCOO-$ | double bond |

TABLE 3

| No. | Compound | $R_1$ | $R_2$ | $R_3$ | $R_4$ | $R_5$ | X |
|---|---|---|---|---|---|---|---|
| 18 | Other derivative | sec-butyl | H | (disaccharide structure with $R_5$, $CH_3$, $CH_3O$ groups) | —H | $(CH_3)_3CCOO-$ | double bond |
| 19 | Other derivative | sec-butyl | $Si(CH_3)_2C(CH_3)_3$ | " | " | $CH(CH_2)_6COO-$ | double bond |
| 20 | Other derivative | sec-butyl | H | " | " | " | double bond |
| 21 | Other derivative | sec-butyl | $Si(CH_3)_2C(CH_3)_3$ | " | " | $CCl_3CH_2OOCCH_2CH_2COO-$ | double bond |
| 22 | Other derivative | sec-butyl | H | " | " | " | double bond |
| 23 | Other derivative | sec-butyl | " | " | " | $HOOCCH_2CH_2COO-$ | double bond |
| 24 | Other derivative | sec-butyl | $Si(CH_3)_2C(CH_3)_3$ | " | " | $(4-NO_2C_6H_4O)COO-$ | double bond |
| 25 | Other derivative | sec-butyl | " | " | " | $H_2NCOO-$ | double bond |
| 26 | Abamectin derivative | sec-butyl | H | " | " | $H_2N-COO-$ | double bond |

TABLE 4

| No. | Compound | $R_1$ | $R_2$ | $R_3$ | $R_4$ | $R_5$ | X |
|---|---|---|---|---|---|---|---|
| 27 | Abamectin derivative | sec-butyl | $Si(CH_3)_2C(CH_3)_3$ | (disaccharide structure with $R_5$, $CH_3$, $CH_3O$ groups) | —H | $(CH_3)_2NCOO-$ | double bond |
| 28 | Abamectin derivative | sec-butyl | H | " | " | " | double bond |
| 29 | Abamectin derivative | sec-butyl | $Si(CH_3)_2C(CH_3)_3$ | " | " | $CH_3CONHCH_2COO-$ | double bond |
| 30 | Abamectin derivative | sec-butyl | H | " | " | " | double bond |

As described above, among these compounds, the compound Nos. 1 to 3 are particularly preferred.

The compound of the formula (I) or a salt thereof contained in the composition of the present invention may be a single compound or mixtures of two or more compounds of the formula (I).

The composition contains at least one of the compounds of the formula (I) or a salt thereof in a concentration of normally 0.1 to 50% by weight, preferably 1 to 10% by weight based on the total amount of the composition.

The composition of the present invention can be molded into conventional compositions or preparations suitable for insecticides such as solutions, wettable powders, emulsions, suspensions, concentrated liquid preparations, tablets, granules, aerosols, powders, pastes, dusts or the like. The composition is preferably an injectable composition such as solutions, suspensions or emulsions, more preferably solutions.

These compositions or preparations can be obtained by conventional methods, for example, by mixing at least one of the compounds of the formula (I) or a salt thereof with an agriculturally acceptable solid or liquid carrier.

If necessary, an appropriate adjuvant (e.g., surfactant, spreader, disperser, stabilizer, etc.) can be added for improvement of dispersibility and other properties of the effective component. In particular, the compound of the formula (I) has very small water-solubility, and therefore it is sometimes difficult to disperse the compound in the trunks of pine trees when a solution of the compound in a solvent is injected into the trunks. In view of this, the composition of the present invention preferably comprises a surfactant in addition to the compound of the formula (I). Such a surfactant improves the water-solubility of the compound, and the composition can easily and effectively be injected into the trunks of pine trees. Thus, the compound can easily be dispersed in the trunks and exhibit stable activity.

As the surfactant, conventional surfactants may be used. Examples of the surfactant which may be used in the invention include anionic surfactants such as alkyl sulfates, alkane sulfonic acids, alkylbenzenesulfonic acids, alkyl phosphates, N-acylsarcosine salts, N-acylalanine salts, succinic acid salts and the like; cationic surfactants such as alkylamines, alkyltrimethyl-ammonium salts, dialkyldimethylammonium salts, alkyldimethylbenzylammonium salts, alkylpyridinium salts; non-ionic surfactants such as polyoxyethylene alkyl ethers, polyoxyethylene alkylphenyl ethers, polyethyleneglycol fatty acid esters, polyoxyethylene polyoxypropylene copolymers, sorbitan fatty acid esters, polyoxyethylenesorbitan fatty acid esters, polyoxyethylenesorbitol fatty acid esters, propylene glycol monofatty acid esters and the like; amphoteric surfactants such as aminocarboxylic acids, carboxybetaines, sulfobetaines and the like.

The amount of the surfactant optionally used in the composition is normally 0.001 to 20% by weight, preferably 0.1 to 10% by weight based on the total weight of the composition.

As the liquid carrier or diluent, any solvent can be used so long as it is easily miscible with water. Examples of such solvents include lower alcohols having 1 to 4 carbon atoms (e.g., methanol, ethanol, etc.), polyhydric alcohols having 2 to 6 carbon atoms (e.g., ethylene glycol, propylene glycol, 1,3-butylene glycol, etc.), ketones (e.g., acetone, etc.), nitriles (e.g., acetonitrile, etc.), ethers (e.g., tetrahydrofuran, ethylene glycol mono-$C_{1-4}$ alkyl (e.g., ethylene glycol monomethyl, ethylene glycol monoethyl, ethylene glycol monopropyl, etc.) ether, etc.) and the like.

Examples of the solid carrier or diluent include botanical materials (e.g., flour, tobacco stalk powder, soybean powder, walnut-shell powder, vegetable powder, saw dust, bran, bark powder, cellulose powder, vegetable extract residue, etc.), fibrous materials (e.g., paper, corrugated cardboard, old rags, etc.), artificial plastic powders, clays (e.g., kaolin, bentonite, fuller's earth, etc.), talc, other inorganic materials (e.g., pyrophyllite, sericite, pumice, sulfur powder, active carbon, etc.), chemical fertilizers (e.g., ammonium sulfate, ammonium phosphate, ammonium nitrate, urea, ammonium chloride, etc.) and the like.

Examples of the spreader or disperser include casein, gelatin, starch powder, carboxymethyl cellulose, gum arabic, alginic acid, lignin, bentonite, molasses, polyvinyl alcohol, pine oil, agar and the like.

Examples of the stabilizer include PAP (a mixture of isopropylphosphate), tricresyl phosphate (TCP), tolu oil, epoxidized oil, surfactants, fatty acids and their esters and the like.

The composition of the present invention may contain other insecticides, fungicides and the like in addition to the above components.

The treatment of pine trees with the composition of the present invention can be carried out by any conventional manner such as injection, atomizing, scattering, spreading or the like to prevent damage caused by the pine wilt nematode disease. Preferably, the composition in the form of solution, suspension or emulsion is injected into the trunks of pine trees. The injection can be carried out, for example, by boring holes in the trunks of pine trees to be treated, and injecting the composition of the present invention through the holes.

The amount of the compound of the formula (I) or a salt thereof to be used in the treatment of pine trees may vary depending upon the subject to be treated, season, age of the tree, severity of the damage and the like, and, generally, injection of 0.1 mg to 100 g, preferably 1 mg to 10 g per one pine tree can provide the desired effect.

The following Examples further illustrate the present invention in detail but are not to be construed to limit the scope thereof.

EXAMPLE 1

Anti-Bursaphelenchus Xylophilus Activity Test

Among the compounds of the formula (I), ivermectin, abamectin and emamectin benzoate were tested and anti-nematode activity of these compounds were noticed. The results are shown in Table 5.

Test Method

Floras of *Botritis cinerea* were formed on the entire surface of a potato-dextrose agar plate to prepare a test plate. A solution of a test compound in a predetermined concentration (0.15 ml) was added to a cotton ball placed on the center of the test plate. Furthermore, a suspension of *Bursaphelenchus xylophilus* (10,000 nematodes/ml, 0.15 ml) was added thereto. After incubation at 25° C. for 5 days, the area of bitten parts of *Botritis cinerea* floras was measured and the anti-nematode activity (%) was calculated from the following equation:
Anti-nematode activity (%) = 100 − area ratio of the bitten part to the plate inner surface area Anti-nematoda activity of compound

| Test compound | Concentration (ppm) | | |
|---|---|---|---|
| | 50 | 5 | 1 |
| Compound of the present invention | | | |
| Ivermectin | 100% | 95% | 35% |
| Abamectin | 100% | 100% | 90% |
| Emamectin benzoate | 100% | 100% | 90% |
| Control compound | | | |
| Morantel tartrate | 100% | 0 | 0 |
| Blank | 0 | 0 | 0 |

EXAMPLE 2

Insecticidal activity Against Japanese Pine Sawyer

Ivermectin, abamectin and emamectin benzoate were tested and insecticidal activity against Japanese pine sawyer of these compounds were noticed. The results are shown in Table 6.

Test Method

A compound to be tested was dissolved in 50% acetone or methanol to prepare a solution of the compound in a predetermined concentration. A one year pine branch was dipped in the solution for 30 seconds and air-dried to prepare a sample to be tested. The sample was given to Japanese pine sawyers and the insecticidal time and the bitten area were measured. The bitten area (S) was calculated from the following equation:

Bitten area $(S)=0.214+0.575 S1$ wherein $S1=\Sigma$(long diameter×short diameter).

| | Insecticidal activity | | | | | | | |
|---|---|---|---|---|---|---|---|---|
| | Acculated mortality (%) Days after feeding pine branch | | | | | | | Bitten area (cm$^2$) |
| Compound | 1 | 2 | 3 | 4 | 5 | 6 | 7 | Average ± S.D. |
| Compound of the present invention | | | | | | | | |
| Ivermectin 100 ppm | 0 | 0 | 40 | 90 | 90 | 100 | — | 0.51 ± 0.10 |
| Abamectin 100 ppm | 0 | 0 | 20 | 50 | 50 | 100 | — | 0.43 ± 0.13 |
| Emamectin benzoate 100 ppm | 0 | 20 | 50 | 100 | — | — | — | 0.50 ± 0.10 |
| Control compound | | | | | | | | |
| Mesulfenfos 100 ppm | 0 | 70 | 100 | — | — | — | — | 0.95 ± 0.6 |
| Morantel tartrate 100 ppm | 0 | 0 | 0 | 0 | 0 | 0 | 0 | 9.0 ± 4.3 |
| Blank | 0 | 0 | 0 | 0 | 0 | 0 | 0 | 10.0 ± 3.0 |

EXAMPLE 3

Test for Preventing Wilting by Using Pine Nursery Stock

Ivermectin, abamectin and emamectin benzoate were tested for the prevention of wilting by using the fifth year pine nursery stock. The results are shown in Table 8.

Test Method

A preparation shown in Table 7 was injected into the trunk of the pine. After about 2 weeks, a suspension of strong toxic *Bursphelenchus xylophilus* (S6.1) (10,000 nematodes/ml) was inoculated. Then, the effect on wilting was evaluated after about 2 months.

| Component | Ivermectin preparation | Abamectin preparation | Emamectin benzoate preparation |
|---|---|---|---|
| Ivermectin | 2.0 g | — | — |
| Abamectin | — | 2.0 g | — |
| Emamectin benzoate | — | — | 2.0 g |
| Polyoxyethylene hardened castor oil | 6.0 g | 6.0 g | 6.0 g |
| Methanol | 70 ml | 70 ml | 70 ml |
| Distilled water | up to 100 ml | up to 100 ml | up to 100 ml |

| | Amount of Active component | Number of trees tested | Number of wilt trees |
|---|---|---|---|
| Preparation of the present invention | | | |
| Ivermectin preparation | 20 mg | 10 | 0 |
| | 5 mg | 10 | 0 |
| | 1 mg | 10 | 0 |
| Abamectin preparation | 20 mg | 10 | 0 |
| | 5 mg | 10 | 0 |
| | 1 mg | 10 | 0 |
| Emamectin benzoate preparation | 20 mg | 10 | 0 |
| | 5 mg | 10 | 0 |
| | 1 mg | 10 | 1 |
| Control preparation | | | |
| Morantel tartrate preparation | 20 mg | 10 | 1 |
| | 5 mg | 10 | 8 |
| | 1 mg | 10 | 9 |
| (Greenguard solution (trade name)) | | | |
| Blank (not treated with compound) | — | 10 | 10 |

EXAMPLE 4

Test for Preventing Maturation Feeding by Japanese Pine Sawyers by Injection into the Trunk of Pine Tree Ivermectin, abamectin and emamectin benzoate were tested for the prevention of maturation feeding by Japanese pine sawyers by injection into the fifth year pine nursery stock. The results are shown in Table 9.

Test Method

The preparation of the above Table 7 was injected into the trunk of pine tree. After one month, the one year young branch was cut off and given to Japanese pine sawyers. The insecticidal time and the bitten area (S) were calculated from the following equation:

Bitten area (S)=0.214+0.575S1 wherein S1=Σ(long diameter×short diameter)

| | | Insecticidal activity | | | | | |
|---|---|---|---|---|---|---|---|
| | | (n = 10) | | | | | |
| | Amount of | Accumulated mortality (%) | | | | | Bitten area (cm²) |
| Com- | active | Days after feeding pine branch | | | | | Average ± |
| pound | component | 1 | 2 | 3 | 4 | 5 | S.D. |
| Compound of the present invention | | | | | | | |
| Ivermectin preparation | 20 mg | 0 | 0 | 30 | 80 | 100 | 0.98 ± 0.37 |
| Abamectin preparation | 20 mg | 0 | 0 | 40 | 100 | — | 0.73 ± 0.33 |
| Emamectin benzoate preparation | 20 mg | 0 | 20 | 100 | — | — | 0.62 ± 0.28 |
| Blank (not treated with compound) | | 0 | 0 | 0 | 0 | 0 | 9.85 ± 3.25 |

EXAMPLE 5

Test for Preventing Wilting

Ivermectin, abamectin and emamectin benzoate were tested for the prevention of wilting by using the tenth year pine nursery stock. The results are shown in Table 10.

Test Method

The preparation of the above Table 7 was injected into the trunk of pine tree. After about 2 weeks, a suspension of strong toxic *Bursphelenchus xylophilus* (S6.1) (100,000 nematodes/ml) was inoculated. Then, the effect on wilting was evaluated after about 3 months.

| | Amount of Active component | Number of trees tested | Number of wilt trees |
|---|---|---|---|
| Preparation of the present invention | | | |
| Ivermectin preparation | 500 mg | 10 | 0 |
| | 100 mg | 10 | 0 |
| | 10 mg | 10 | 0 |
| Abamectin preparation | 500 mg | 10 | 0 |
| | 100 mg | 10 | 0 |
| | 10 mg | 10 | 2 |
| Emamectin benzoate preparation | 500 mg | 10 | 0 |
| | 100 mg | 10 | 0 |
| | 10 mg | 10 | 1 |
| Control preparation | | | |
| Morantel tartrate preparation (Greenguard solution (trade name)) | 500 mg | 10 | 0 |
| | 100 mg | 10 | 3 |
| | 10 mg | 10 | 8 |
| Blank (not treated with compound) | — | 10 | 10 |

Object of the Invention

The present invention provides with the composition and the method for the prevention of the pine wilt. By the treatment of pine trees with the composition of the present invention. The risk of the infection with pine wilt nematodes is reduced. Further, even if pine trees are infected with pine wilt nematodes, the pine wilt nematodes can be killed before the pine wilt nematodes start action in the trunks of the pine trees, whereby the wilting of the pines by the pine wilt nematode disease is prevented.

What is claimed is:

1. A method for preventing or treating pine wilting disease which comprises injecting into the trunk of a pine tree in need thereof a compound of the formula (I):

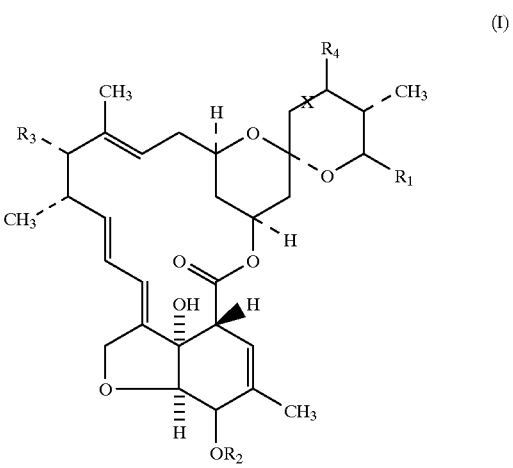

(I)

wherein:

$R_1$ is alkyl, cycloalkyl or alkenyl;

$R_2$ is hydrogen, alkyl, alkanoyl or alkylsilyl;

$R_3$ is hydrogen or optionally substituted hydroxyl;

$R_4$ is hydrogen, hydroxyl or alkoxyimino;

the carbon-carbon bond X represents a single bond or double bond, provided that, when $R_4$ is alkoxyimino, X represents a single bond, and when $R_1$ is methyl or ethyl and $R_2$, $R_3$ and $R_4$ are hydrogen, X represents a double bond; or a salt thereof, in an amount which is nematocidally and insecticidally effective in controlling both the pine wilt nematode Bursaphelenchus xylophilus and the pine sawyer beetle *Monochamus alternatus*.

2. The method of claim 1 wherein the compound of the formula (I), $R_1$ is isopropyl or sec-butyl.

3. The method of claim 1 wherein the compound of the formula (I), $R_2$ is hydrogen.

4. The method of claim 1 wherein the compound of the formula (I), $R_3$ is a group of the formula (II) or formula (III):

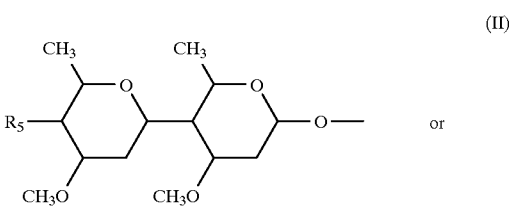

(II)

or

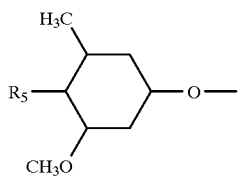

(III)

wherein $R_5$ is oxo;

optionally substituted hydroxyl; or

—$NR_6R_7$ wherein $R_6$ and $R_7$ are each independently hydrogen, lower alkyl, lower alkanoyl, optionally substituted benzenesulfonyl or lower alkylsulfonyl.

5. The method of claim 4 wherein the compound of the formula (I), $R_3$ is a group of the formula (II) wherein $R_5$ is hydroxyl or methylamino.

6. The method of claim 1 wherein the compound of the formula (I), $R_4$ is hydrogen.

7. The method of claim 1 wherein the compound of the formula (I), $R_1$ is sec-butyl or isopropyl, $R_2$ is hydrogen, $R_3$ is a group of the formula (II)

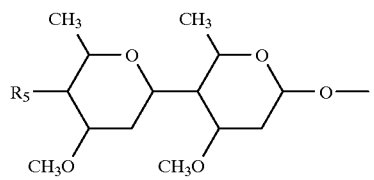

(II)

$R_4$ is hydrogen, $R_5$ is hydroxyl, and X is a single bond.

8. The method of claim 1 wherein the compound of the formula (I), $R_1$ is sec-butyl or isopropyl, $R_2$ is hydrogen, $R_3$ is a group of the formula (II)

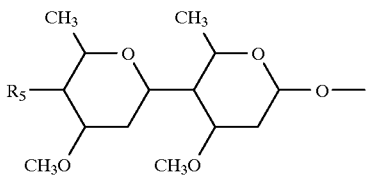

(II)

$R_4$ is hydrogen, $R_5$ is hydroxyl, and X is a double bond.

9. The method of claim 1 wherein the compound of the formula (I), $R_1$ is sec-butyl or isopropyl, $R_2$ is hydrogen, $R_3$ is a group of the formula (II)

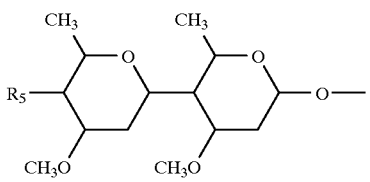

(II)

$R_4$ is hydrogen, $R_5$ is methylamino, and x is a double bond.

10. The method of claim 1 wherein the compound is ivermectin.

11. The method of claim 1 wherein the compound is abamectin.

12. The method of claim 1 wherein the compound is emamectin benzoate.

13. The method of claim 1 wherein the compound is moxidectin.

14. The method of claim 1 wherein the compound is doramectin.

* * * * *